(12) United States Patent
Simon et al.

(10) Patent No.: US 8,552,245 B2
(45) Date of Patent: Oct. 8, 2013

(54) METHOD FOR TREATING A CRACKED GAS STREAM FROM A HYDROCARBON PYROLYSIS INSTALLATION AND INSTALLATION ASSOCIATED THEREWITH

(75) Inventors: Yvon Simon, Andresy (FR); Jean-Paul Laugier, Paris (FR)

(73) Assignee: Technip France (FR)

( * ) Notice: Subject to any disclaimer, the term of this patent is extended or adjusted under 35 U.S.C. 154(b) by 0 days.

(21) Appl. No.: 13/638,118

(22) PCT Filed: Mar. 28, 2011

(86) PCT No.: PCT/FR2011/050671
§ 371 (c)(1),
(2), (4) Date: Dec. 15, 2012

(87) PCT Pub. No.: WO2011/124818
PCT Pub. Date: Oct. 13, 2011

(65) Prior Publication Data
US 2013/0102827 A1   Apr. 25, 2013

(30) Foreign Application Priority Data

Mar. 29, 2010   (FR) ...................................... 10 52271

(51) Int. Cl.
*C07C 7/04*   (2006.01)
(52) U.S. Cl.
USPC .............................. 585/809; 585/807; 62/631

(58) Field of Classification Search
None
See application file for complete search history.

(56) References Cited

U.S. PATENT DOCUMENTS

| 4,629,484 A | 12/1986 | Kister |
| 5,253,479 A | 10/1993 | Di Cintio et al. |

FOREIGN PATENT DOCUMENTS

WO   WO 2007/018510 A1   2/2007

OTHER PUBLICATIONS

International Search Report and Written Opinion dated Aug. 23, 2012 issued in connection with International Patent Application No. PCT/FR2011/050671.

*Primary Examiner* — Tam M Nguyen
(74) *Attorney, Agent, or Firm* — Ostrolenk Faber LLP

(57) ABSTRACT

This method includes the separation of an upstream partly condensed cracked gas stream in an intermediate separator (44B) in order to recover an intermediate liquid (136), and an intermediate cracked gas stream (138) and the introduction of the intermediate liquid (140) into an intermediate demethanization column (68). The method comprises the sampling of a portion of the intermediate liquid (136) and the expansion of at least one first fraction (194) obtained from the sampled portion (190). It comprises the putting of the first expanded fraction in a heat exchange relationship with the intermediate head stream (146) from the column (68) for at least partly condensing the intermediate head stream (146). The method includes the separation of the intermediate partly condensed head stream in a first reflux separator (76) in order to form a liquid stream (148) introduced into the intermediate column (68) and a combustible gas stream (150).

17 Claims, 1 Drawing Sheet

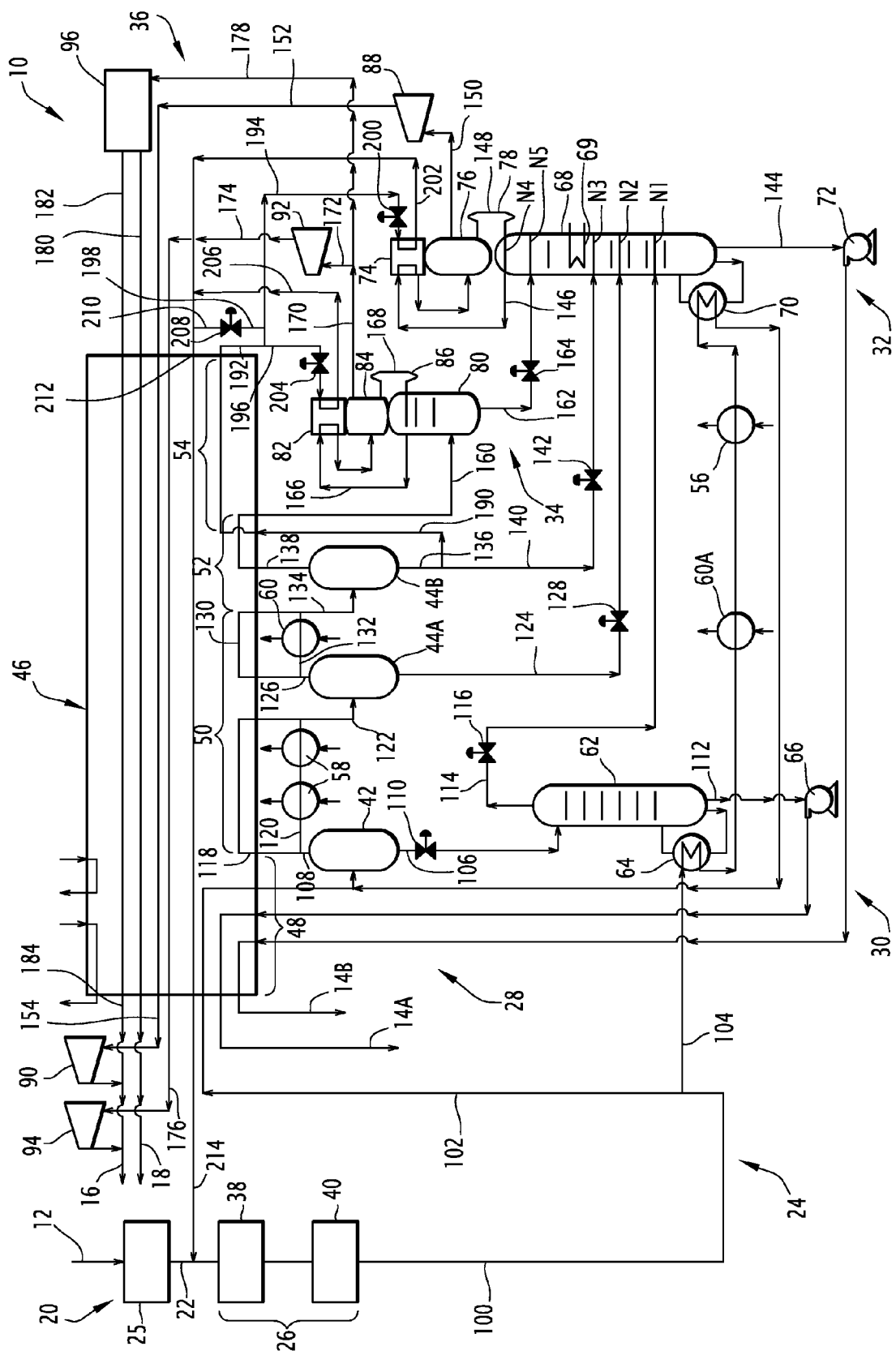

METHOD FOR TREATING A CRACKED GAS STREAM FROM A HYDROCARBON PYROLYSIS INSTALLATION AND INSTALLATION ASSOCIATED THEREWITH

CROSS REFERENCE TO RELATED APPLICATIONS

The present application is a 35 U.S.C. §371 National Phase conversion of PCT/FR2011/050671, filed Mar. 28, 2011, which claims benefit of French Application No. 10 52271, filed Mar. 29, 2010, the disclosures of which are incorporated herein by reference. The PCT International Application was published in the French language.

TECHNICAL FIELD

The present invention relates to a method for treating a cracked gas stream from a hydrocarbon pyrolysis installation, comprising the following steps:
  upstream cooling and partial condensation of a crude cracked gas stream in at least one upstream heat exchange region;
  separating the partly condensed crude gas stream in at least one upstream separator in order to recover an upstream liquid and an upstream cracked gas stream;
  introducing the upstream liquid into an upstream demethanization column for recovering at the head of the upstream column, an upstream head stream rich in methane and, at the bottom of the upstream column, a first liquid stream rich in $C_2^+$ hydrocarbons;
  intermediate cooling and partial condensation of the upstream cracked gas stream in at least one intermediate heat exchange region;
  separating the partly condensed upstream cracked gas stream in at least one intermediate separator for recovering at least one intermediate liquid and one intermediate cracked gas stream;
  introducing the or each intermediate liquid into an intermediate demethanization column in order to recover at the head of the intermediate column, an intermediate head stream, and at the bottom of the intermediate column, a second liquid stream rich in $C_2^+$ hydrocarbons;
  introducing at least one portion of the upstream head stream from the upstream column into the intermediate column;
  downstream cooling and partial condensation of the intermediate cracked gas stream in at least one downstream heat exchange region;
  separating the intermediate partly condensed cracked gas stream in a downstream separation assembly for recovering a downstream liquid and a downstream treated gas stream;
  introducing the downstream liquid into the intermediate demethanization column.

The cracked gas is obtained from a hydrocarbon pyrolysis installation, such as a vapocracking furnace. The gas introduced into the pyrolysis installation advantageously contains ethane, propane, butane, naphtha and/or gasoil alone or as a mixture.

BACKGROUND OF THE INVENTION

The method of the aforementioned type is intended to treat cracked gas in order to be able to extract more than 99.5% by moles of the ethylene contained in the cracked gas, and to obtain an ethylene-rich cut has a content greater than 99.95% by moles of ethylene.

A method of the aforementioned type with which such performances may be obtained is for example described in U.S. Pat. No. 5,253,479.

This method is applied for treating very large volumes of cracked gas, for example greater than 50 metric tons per hour, notably greater than 100 metric tons per hour.

In order to guarantee both very high purity of the produced ethylene stream and a maximum ethylene recovery rate, it is necessary to cool the cracked gas stepwise down to temperatures below −100° C. and notably below −120° C.

For this purpose, the cracked gas is successively cooled in increasingly cold heat exchange regions. The cracked gas is partly condensed in each heat exchange region.

At the outlet of each heat exchange region, the condensed liquid containing the $C_2^+$ hydrocarbons is recovered.

The liquids condensed at a higher temperature are sent into an upstream demethanization column in order to recover at the bottom a first cut rich in $C_2^+$ hydrocarbons.

The intermediate and downstream liquids obtained at lower temperatures are sent into an intermediate demethanization column which produces at the bottom a second cut rich in $C_2^+$ hydrocarbons.

The head stream from the upstream column is introduced into the intermediate column.

In U.S. Pat. No. 5,253,479, in order to further improve recovery of ethylene, the head stream from the intermediate demethanization column is introduced, after cooling, into a third separation column. The bottom of the third column is then partly reintroduced after pumping in a first cryogenic pump, with reflux into the intermediate column. The head of the third column is introduced after cooling and pumping by a second cryogenic pump, into an ethylene absorber which forms the fourth distillation column.

The method described in U.S. Pat. No. 5,253,479 is therefore particularly effective in order to obtain excellent recovery of ethylene.

Taking into account the presence of four distillation columns, and of two cryogenic pumps, the structure of the installation and the energy consumption of the method may nevertheless still be improved.

SUMMARY OF THE INVENTION

An object of the invention is therefore to obtain with minimum investment and simplification of the equipment, a method for treating a cracked gas with which the totality of the ethylene contained in the cracked gas may be quasi extracted, while having improved energy and operating performances.

For this purpose, the subject-matter of the invention is a method of the aforementioned type, characterized in that the method comprises the following steps:
  sampling a portion of an intermediate liquid from an intermediate separator and cooling of the sample portion in an additional heat exchange region;
  expanding at least one first cooling fraction obtained from the sample portion and putting the first expansed cooling fraction in a heat exchange relationship with the intermediate head stream in a first head heat exchanger for condensing at least partly the intermediate head stream;
  separating the intermediate partly condensed head stream in a first reflux separator in order to form a liquid reflux stream introduced into the intermediate column by gravity flow, and a first combustible gas stream;

expanding and heating up the first combustible gas stream by having it pass into at least one region among the additional heat exchange region, the downstream heat exchange region, the intermediate heat exchange region, and the upstream heat exchange region.

The method according to the invention may comprise one or more of the following features, taken individually or according to all technically possible combination(s):

the intermediate column includes an integrated heat exchanger, said or each intermediate liquid being introduced above the integrated heat exchanger;

the method comprises a step for forming the crude cracked gas stream by compression of cracked gas stemming from the pyrolysis installation in at least one compression apparatus, the method comprising the following steps:
  heating up the first cooling fraction in the first head heat exchanger in at least one region among the additional heat exchange region, the downstream heat exchange region, the intermediate heat exchange region and the upstream heat exchange region; and
  introducing the heated-up first cooling fraction into the cracked gas upstream from or within the compression apparatus;

the first combustible gas stream stemming from the first reflux separator is expanded in a first dynamic expansion turbine, and is then heated up in at least one region among the additional heat exchange region, the downstream heat exchange region, the intermediate heat exchange region, and the upstream heat exchange region, the method comprising a step for recompression of the first heated-up combustible stream in at least one first compressor coupled with the first dynamic expansion turbine;

the first combustible gas stream stemming from the first reflux separator is expanded in a static expansion valve;

the downstream separation assembly includes an ethylene absorption column, the method comprising the following steps:
  introducing the partly condensed cracked gas intermediate stream into the ethylene absorption column,
  recovering an additional head gas stream from the ethylene absorption column;
  expanding a second cooling fraction obtained from the portion sampled in the intermediate liquid, and
  putting the second expansed cooling fraction in a heat exchange relationship with the head additional stream in a second head heat exchanger in order to condense at least partly the additional head stream;
  introducing the additional partly condensed head stream into a second reflux separator in order to form a second reflux liquid stream introduced into the ethylene absorption column by gravity flow and a treated gas stream;

the method comprises the following steps:
  forming the crude cracked gas stream by compressing cracked gas from the pyrolysis installation in a compression apparatus;
  heating up the second cooling fraction, downstream from the second head heat exchanger, in at least one region among the additional heat exchange region, the downstream heat exchange region, the intermediate heat exchange region, and the upstream heat exchange region;
  introducing the heated-up second cooling fraction into the cracked gas from the pyrolysis installation, upstream from or within the compression apparatus;

the method comprises the following steps:
  expanding at least one first portion of the treated gas stream in at least one second dynamic expansion turbine,
  heating up after expansion the first portion of the treated gas stream in at least one region among the additional heat exchange region, the downstream exchange region, the intermediate heat exchange region, and the upstream heat exchange region;
  compression of the first heated-up portion in at least one second compressor coupled with the second dynamic expansion turbine;

the method comprises a step for expanding at least one first portion of the treated gas stream in a static expansion valve;

at least one second portion of the treated gas stream is introduced into a hydrogen purification unit in order to produce a hydrogen-rich stream and an auxiliary combustible gas stream and optionally a secondary stream rich in methane;

a third fraction of the sampled portion is expanded, before being directly heated up in at least one region among the additional heat exchange region, the downstream heat exchange region, the intermediate heat exchange region and the upstream heat exchange region;

the method includes the following steps:
  separation of the crude cracked gas stream into a first crude cracked gas fraction and into a second crude cracked gas fraction;
  upstream cooling and partial condensation of the first crude cracked gas fraction in the upstream heat exchange region;
  cooling the second crude cracked gas fraction in an upstream reboiling exchanger, by heat exchange with an upstream reboiling stream from the upstream column, and then cooling the second crude cracked gas fraction in an intermediate reboiling exchanger by heat exchange with an intermediate reboiling stream from the intermediate column;
  forming the partly condensed crude cracked gas stream by mixing the first cooled crude cracked gas fraction and the second cooled crude cracked gas fraction;

the temperature of the partly condensed crude cracked gas before its introduction into the upstream separator is below −25° C., the temperature of the upstream partly condensed cracked gas stream before its introduction into the intermediate separator is below −60° C., and the temperature of the partly condensed intermediate stream before its introduction into the downstream separation assembly is below −115° C.

The subject-matter of the invention is further an installation for treating a cracked gas stream from a hydrocarbon pyrolysis installation, of the type comprising:

upstream cooling and partial condensation means for a crude cracked gas stream comprising at least one upstream heat exchange region;

means for separating the partly condensed crude cracked gas stream comprising at least one upstream separator for recovering an upstream liquid and an upstream cracked gas stream;

an upstream demethanization column and means for introducing the upstream liquid into the upstream column in order to recover at the head of the upstream column, an upstream head stream rich in methane and, at the bottom of the upstream column, a first liquid stream rich in $C_2^+$ hydrocarbons;

intermediate cooling and partial condensation means for the upstream cracked gas stream comprising at least one intermediate heat exchange region;

means for separating the upstream partly condensed cracked gas stream comprising at least one intermediate separator for recovering at least one intermediate liquid and one intermediate cracked gas stream;

an intermediate demethanization column and means for introducing the or each intermediate liquid into the intermediate column in order to recover at the head of the intermediate column, an intermediate head stream, and at the bottom of the intermediate column, a second liquid stream rich in $C_2^+$ hydrocarbons;

means for introducing at least one portion of the upstream head stream from the upstream column into the intermediate column;

downstream cooling and partial condensation means for the intermediate cracked gas stream comprising at least one downstream heat exchange region;

means for separating the intermediate partly condensed cracked gas stream comprising a downstream separation assembly for recovering a downstream liquid and a downstream treated gas stream;

means for introducing the downstream liquid into the intermediate demethanization column;

characterized in that the installation comprises:

means for sampling a portion of an intermediate liquid from an intermediate separator and means for cooling the sampled portion comprising an additional heat exchange region;

means for expanding at least one first cooling fraction obtained from the sampled portion and means for putting the first expanded cooling fraction in a heat exchange relationship with the intermediate head stream comprising a first head heat exchanger for at least partly condensing the intermediate head stream;

means for separating the intermediate partly condensed head stream comprising a first reflux separator for forming a reflux liquid stream introduced into the intermediate column and a first combustible gas stream;

means for heating up the first combustible gas stream comprising means for passing into at least one region among the additional heat exchange region, the downstream heat exchange region, the intermediate heat exchange region and the upstream heat exchange region.

The installation according to the invention may comprise one or more of the following features, taken individually or according to all technically possible combination(s):

it comprises:
means for forming the crude cracked gas stream by compression of cracked gas from the pyrolysis installation including at least one compression apparatus;
means for heating up the first downstream cooling fraction of the first head heat exchanger comprising means for passing into at least one region among the additional heat exchange region, the downstream heat exchange region, the intermediate heat exchange region and the upstream heat exchange region; and
means for introducing the first heated-up cooling fraction into the cracked gas upstream from or within the compression apparatus;

the downstream separation assembly includes an ethylene absorption column, the installation comprising:

means for introducing the intermediate partly condensed cracked gas stream into the ethylene absorption column, means for recovering an additional head gas stream from the ethylene absorption column;

means for expanding a second cooling fraction obtained from the sampled portion; and means for putting the second expansed cooling fraction in a heat exchange relationship with the additional head stream comprising a second head heat exchanger for at least partly condensing the additional head stream;

means for separating the additional partly condensed head stream comprising a second reflux separator for forming a second reflux liquid stream introduced into the ethylene absorption column and a treated gas stream; and the installation comprises:
means for forming the crude cracked gas stream by compressing cracked gas from the pyrolysis installation including at least one compression apparatus;
means for heating up the second downstream cooling fraction of the second head heat exchanger, comprising means for passing into at least one region among the additional heat exchange region, the downstream heat exchange region, the intermediate heat exchange region, and the upstream heat exchange region;
means for introducing the heated-up second cooling fraction into the cracked gas from the pyrolysis installation, upstream from or within the compression apparatus.

BRIEF DESCRIPTION OF THE DRAWINGS

The invention will better understood upon reading the description which follows, only given as an example and made with reference to the appended drawing, wherein:

the single FIGURE is a functional block diagram of a first treatment installation according to the invention, intended for applying a first method according to the invention.

DESCRIPTION OF PREFERRED EMBODIMENTS

In all of the following, a same reference designates a stream flowing in a conduit and the conduit which conveys this stream. Moreover, unless indicated otherwise, the percentages are molar percentages and the pressures are meant to be in relative bars.

A first vapocracking unit 10 according to the invention is illustrated in the single FIGURE.

This unit 10 produces, from a load 12, streams 14A, 14B rich in $C_2^+$ intended to form an ethylene-rich cut, a combustible gas 16 and a hydrogen-rich stream 18.

The unit 10 comprises a hydrocarbon pyrolysis installation 20 producing crude cracked gas 22 and an installation 24 for treating the crude cracked gas 22.

The pyrolysis installation 20 includes several vapocracking furnaces 25. The vapocracking furnaces 25 are capable of circulating the load 12 in order to heat it to a temperature above 800° C. This causes thermal cracking of the hydrocarbon molecules contained in the load 12 in order to form the crude cracked gas 22.

The fractionation installation 24 successively includes a compression assembly 26 and an assembly 28 for cooling and successively separating the cracked gas.

The installation 24 further comprises an upstream distillation assembly 30, an intermediate distillation assembly 32 and an additional ethylene absorption assembly 34. The installation 24 also comprises a downstream assembly 36 for expanding and heating up the combustible gas.

The cooling and compression assembly 26 comprises a cooling apparatus (not shown), a primary compressor 38 and a secondary compressor 40, the secondary compressor 40 being located downstream from the primary compressor 38.

The cooling and separation assembly 28 comprises an upstream separating flask 42, a first intermediate separating flask 44A, a second intermediate separating flask 44B. It further comprises an integrated heat exchanger including a cold box 46. The cold box 46 comprises an upstream heat exchange region 48, an intermediate heat exchange region 50, a downstream heat exchange region 52 and an additional heat exchange region 54, which are increasingly cold.

The cooling assembly 28 further comprises a refrigeration cycle with propane or propylene having an upstream cycle exchanger 56 and a refrigeration cycle with ethylene comprising a first assembly of intermediate cycle exchangers 58 and a second assembly of intermediate cycle exchangers 60. Optionally, the cooling assembly 28 further includes an additional upstream cooling exchanger 60A fed with a coolant fluid formed by an intermediate reboiling stream from a $C_2$ hydrocarbon separator or by an ethane stream intended to be vaporized.

The upstream distillation assembly 30 includes an upstream distillation column 62, an upstream column bottom reboiler 64 and an upstream column bottom pump 66.

The column 62 operates at a pressure comprised between 10 bars and 14 bars. It includes for example between 14 and 20 theoretical plates.

The intermediate distillation assembly 32 includes an intermediate demethanization column 68, an integrated exchanger 69, an intermediate reboiling exchanger 70 and an intermediate column pump 72.

The intermediate assembly 32 further includes a first reflux heat exchanger 74 and a first reflux separator flask 76 connected to the column 68 through a conduit 78 for liquid downflow, conformed in order to prevent passing of gases from the column 62 to the flask 76. This assembly 32 avoids the installation of reflux cryogenic pumps.

The column 68 operates at a pressure comprised between 10 bars and 14 bars. It includes between 22 and 28 theoretical plates for example.

The integrated exchanger 69 is placed in the column 68 between an upper portion and a lower portion of the column 69.

The downstream distillation assembly 34 comprises an ethylene absorption column 80, a second reflux heat exchanger 82 and a second reflux separating flask 84 connected to the ethylene absorption column 80 through a conduit 86 for liquid downflow, conformed in order to prevent the passing of gases from the column 80 to the flask 84. This assembly 34 avoids the installation of reflux cryogenic pumps.

As this will be seen below, the reflux cryogenic pump present in U.S. Pat. No. 5,253,479 may be suppressed from the column 68, which leads to the production of a liquid required for ethylene absorption in the assembly 34 by means of the exchanger 82.

The column 80 operates at a pressure comprised between 30 bars and 40 bars. It includes between 4 and 8 theoretical plates for example.

The downstream assembly 36 comprises a first dynamic expansion turbine 88 coupled with a first compressor 90, a second dynamic expansion turbine 92 coupled with a second compressor 94 and a hydrogen purification unit 96.

A first method according to the invention applied in unit 10 will now be described.

Initially, the load 12 includes ethane, propane, butane, naphtha and/or gas oil alone or as a mixture. It is introduced into the vapocracking furnaces 25 in order to be heated to a temperature above 800° C. and to undergo thermal cracking.

A crude cracked gas is extracted from the furnaces at a temperature above 800° C., and is then rapidly cooled in order to generate the flow 22 at a temperature above 160° C. and at a pressure above 1 bar.

The gas 22 is then cooled and introduced into the primary compressor 38 so as to be compressed to a pressure above 10 bars, and then in the secondary compressor 40 so as to be compressed therein to a pressure above 30 bars. The compressed crude cracked gas stream 100 is then separated into a first crude cracked gas fraction 102 and into a second crude cracked gas fraction 104.

The first crude cracked gas fraction 102 is conveyed up to the cold box 46 so as to be cooled therein down to a temperature below −25° C. and notably comprised between −30° C. and −40° C. so as to be partly condensed therein in the upstream heat exchange region 48.

The second crude cracked gas fraction 104 is successively cooled in the upstream reboiling exchanger 64, in the optional cooling exchanger 60A, in the upstream cycle exchanger with propane or propylene 56, before being again cooled in the intermediate reboiling exchanger 70 in order to attain a temperature below −25° C. and notably comprised between −30° C. and −40° C. The fraction 104 is further partly condensed.

The temperature of the stream 104 upstream from the exchanger 64 is comprised between −2° C. and −12° C. and the temperature of the stream 104 downstream from reboiling in the exchanger 70 is comprised between −30° C. and −40° C.

The ratio of the molar flow rate of the first fraction 102 to the molar flow rate of the second fraction 104 is for example comprised between 0.25 and 0.40.

The first fraction 102 and the second fraction 104 forming a partly condensed cracked gas stream are then introduced into the upstream separating flask 42 so as to be separated therein into an upstream liquid 106 and into an upstream gas stream 108 of cracked gas.

The upstream liquid 106 contains between 45% and 55% by moles of $C_2$ hydrocarbons present in the crude cracked gas 22 and between 85% and 95% by moles of $C_3^+$ hydrocarbons contained in the crude cracked gas 22.

The upstream liquid 106 is then expanded in a first static expansion valve 110 so as to be introduced to an upper level of the upstream demethanization column 62.

The upstream column 62 produces at its bottom a first liquid stream 112 rich in $C_2^+$ hydrocarbons which is conveyed up to the upstream pump 66 in order to produce a first stream 14A rich in $C_2^+$ hydrocarbons which is pumped. The first stream 14A is intended to be conveyed towards a deethanization column in order to extract the ethylene-rich cut therefrom, which will then be purified in order to attain an ethylene content of greater than 99.95%.

The molar content of $C_2$ hydrocarbons in the first stream 112 is greater than 50%. The molar content of methane in the first stream 112 is less than 0.01%.

The upstream column 62 further produces a head gas stream 114 rich in methane. The head gas stream 114 is introduced into the intermediate column 68 at a lower level $N_1$ of this column after passing into the valve 116.

A first portion 118 of the upstream cracked gas stream 108 is then introduced into the intermediate heat exchange region 50 in order to be cooled therein down to a temperature below −60° C. and notably comprised between −65° C. and −76° C. and in order to be partly condensed therein.

A second portion 120 of the upstream cracked gas stream 108 is successively introduced into the first assembly of intermediate exchangers 58 of the ethylene cycle so as to be cooled therein down to a temperature below −60° C. and for example comprised between −65° C. and −76° C., and in order to be partly condensed therein.

The ratio of the flow rate of the first portion 118 to the flow rate of the second portion 120 is for example comprised between 0.15 and 0.25.

The first portion 118 and the second portion 120 are then mixed in order to form an upstream partly condensed cracked gas 122 which is introduced into the first intermediate separating flask 44A. The molar liquid fraction in the upstream partly condensed cracked gas stream 122 is greater than 25%.

The stream 122 is then separated in the first intermediate flask 44A into a first intermediate liquid 124 and into a first intermediate cracked gas stream 126.

The first intermediate liquid 124 is expanded in a third static expansion valve 128 down to a pressure below 14 bars before being introduced to a level $N_2$ of the intermediate column located above the level $N_1$.

The first intermediate liquid 124 includes between 60% and 75% of the $C_2$ hydrocarbons contained in the crude cracked gas 22 and between 10% by moles and 15% by moles of the $C_3^+$ hydrocarbons contained in the crude cracked gas 22.

A first portion 130 of the first intermediate stream of cracked gas 126 is then introduced into the intermediate heat exchange region 50 so as to be cooled therein to a temperature below −90° C. and notably comprised between −92° C. and −99° C. and in order to be partly condensed therein.

A second portion 132 of the intermediate stream 126 is introduced into the second intermediate exchanger assembly 60 of the refrigeration cycle with ethylene in order to be cooled therein to a temperature below −90° C. and notably comprised between −92° C. and −99° C. and in order to be partly condensed therein.

The first portions 130 and 132 are then mixed in order to form a first intermediate stream 134 of partly condensed cracked gas. The molar liquid content of the stream 134 is greater than 15%.

The stream 134 is then introduced into the second intermediate separating flask 44B so as to be separated therein into a second intermediate liquid 136 and into a second intermediate stream 138 of cracked gas.

The second intermediate liquid 136 contains between 55% molar and 65% molar of $C_2$ hydrocarbons contained in the crude cracked gas stream 22 and between 0.5% molar and 1.5% molar of $C_3^+$ hydrocarbons contained in the crude cracked gas 22.

A first portion 140 of the second intermediate liquid 136 is then expanded in a fourth static expansion valve 142 down to a pressure below 14 bars in order to be introduced to a level $N_3$ of the intermediate column 68 located above the level $N_2$.

The level $N_3$ is located below the integrated exchanger 69.

The intermediate demethanization column 68 produces at its bottom, a second bottom stream 144 rich in $C_2^+$ hydrocarbons. The stream 144 is pumped through the intermediate pump 72 up to a pressure above 20 bars in order to form a second stream 14B rich in $C_2^+$ intended to be sent to the deethanization column.

The molar content of $C_2^+$ hydrocarbons in the stream 144 and in the stream 14B is greater than 90%. The molar methane content in the stream 144, 14B is less than 0.01% molar.

The intermediate column 68 produces at its head, an intermediate head stream 146 which is cooled and partly condensed down to a temperature below −115° C., for example comprised between −118° C. and −123° C., in the first reflux heat exchanger 74.

The intermediate partly condensed head stream is then introduced into the first reflux flask 76 so as to be separated therein into a first liquid reflux stream 148 and a first high pressure combustible gas stream 150.

The first reflux stream 148 is introduced to a head level $N_4$ of the column 68 through the conduit 78. The level $N_4$ is located above the integrated exchanger 69. This reflux system by gravity flow avoids the installation of a cryogenic pump.

The first combustible gas stream 150 contains more than 90% by moles of methane and less than 0.1% by moles of $C_2$ hydrocarbons. The stream 150 is then advantageously expanded in the first dynamic expansion turbine 88 down to a pressure for example of less than 4.5 bars for forming a low pressure combustible stream 152 cooled to a temperature below −135° C.

The stream 152 is then introduced into the cold box 46 so as to be successively heated up therein in the additional medium 54, in the downstream region 52, in the intermediate region 50 and in the upstream heated exchange region 48, with heat exchange with the streams respectively flowing in these regions.

The first heated-up combustible stream 154 from the first heat exchange region 48 is then brought into the first compressor 90 coupled with the turbine 88 so as to be compressed up to a pressure above 5.0 bars and in order to form a portion of the combustible gas stream 16.

In one alternative, the assembly formed by the expansion turbine 88 and the compressor 90 is replaced with a global static expansion valve.

The second intermediate stream 138 of cracked gas stemming from the second intermediate flask 44B is then cooled and partly condensed in the downstream exchange region 52 of the cold box 46 in order to form an intermediate stream 160 of partly condensed cracked gas.

The stream 160 is then introduced to a lower level of the ethylene absorption column 80 at a temperature below −110° C. and notably comprised between −115° C. and −120° C.

The ethylene absorption column 80 operates at a pressure for example comprised between 30 bars and 36 bars.

The additional bottom stream 162 produced at the bottom of the column 80 is then expanded down to a pressure below 15 bars through a fifth static expansion valve 164 before being introduced to a level $N_5$ of the intermediate demethanization column 68 located between the level $N_3$ and the level $N_4$.

This stream 162 contains between 3.0% and 5.0% by moles of $C_2$ hydrocarbons present in the cracked gas 22 and between 0.01% and 0.04% by moles of $C_3^+$ hydrocarbons present in the crude cracked gas 22.

The additional head stream 166 produced in the column 80 is introduced into the second reflux heat exchanger 82 so as to be cooled to a temperature below −115° C. and notably comprised between −118° C. and −130° C. and to be partly condensed.

The additional partly condensed head stream 166 is then introduced into the second reflux separating flask 84 in order to form a second liquid reflux stream 168 and a high pressure treated gas stream 170.

The second liquid reflux stream 168 is introduced with reflux into the ethylene absorption column 80 through the conduit 86. This reflux absorption system by gravity flow avoids the installation of a cryogenic pump.

A first portion 172 of the treated stream 170 is sent to the second dynamic expansion turbine 92 so as to be expanded therein to a pressure below 4.5 bars and to form a second low pressure combustible gas stream cooled to a temperature below −140° C.

The stream 174 is then successively heated up through the additional region 54, the downstream region 52, the intermediate region 50 and the upstream heat exchange region 48 inside the cold box 46 in order to form a second heated-up combustible gas stream 176.

The second stream 176 is then introduced into the second compressor 94 in order to form a portion of the combustible gas 16.

In one alternative, the expansion turbine 92 and compressor 94 assembly is replaced by a global static expansion valve.

A second portion 178 of the treated gas 170 is conveyed up to the hydrogen purification cryogenic unit 96 in order to form a hydrogen-rich stream 180 and a third low pressure combustible stream 182.

The hydrogen content in the hydrogen-rich stream 180 produced by the unit 96 is greater than 90% molar. The temperature of the stream 180 is below −125° C.

The stream 180 is then successively passed into the additional heat exchange region 54, into the downstream heat exchange region 52, into the intermediate heat exchange region 50 and into the upstream heat exchange region 48 of the cold box 46 so as to be heated up therein by heat exchange with streams respectively flowing in these regions and in order to form the hydrogen-rich stream 18.

The third combustible stream 182 from the unit 96 has a temperature below −125° C. This stream 182 is then successively passed into the additional heat exchange region 54, into the downstream heat exchange region 52, into the intermediate heat exchange region 50, and then into the upstream heat exchange region 48 for heating it up by heat exchange with streams respectively flowing in these regions.

The third heated-up combustible stream 184 is then mixed with the first heated-up combustible stream 154, after its compression in the compressor 94 and with the second heated-up combustible stream 176 in order to form a portion of the combustible stream 16.

According to the invention, the frigories required for condensing the intermediate gas head stream 146 stemming from the intermediate column 68 are provided by the heat exchange with a stream flowing in a semi-open cycle of the JOULE-THOMPSON type.

In an alternative (not shown), the frigories required for condensing the intermediate gas head stream 146 stemming from the intermediate column 68 are partly provided in the same exchanger 74 by heat exchange either with the low pressure combustible stream 152 or with the second combustible gas stream 174, respectively obtained at the exhaust of the expansion turbine 88 or at the exhaust of the expansion turbine 92, in addition to the semi-open cycle of the JOULE-THOMPSON type.

Further, the frigories required for condensing the head stream 166 stemming from the absorption column 80 are provided by heat exchange with a stream flowing in a semi-open cycle of the JOULE-THOMPSON type.

In one alternative (not shown), the frigories required for condensing the head stream 166 from the absorption column 80 are partly provided by heat exchange in the same exchanger 82 either with the low pressure combustible stream 152 or with the second combustible gas stream 174, respectively obtained at the exhaust of the expansion turbine 88 or at the exhaust of the expansion turbine 92, in addition to the semi-open cycle of the JOULE-THOMPSON type.

For this purpose, a second portion 190 of the second intermediate liquid 136 from the separating flask 44B is sampled and cooled in the additional heat exchange region 54 down to a temperature below −125° C., in order to form a second cooled sample portion 192.

The second cooled sampled portion 192 is then separated into a first cooling fraction 194 of the first reflux heat exchanger 74, into a second cooling fraction 196 of the second reflux heat exchanger 82 and into a third extra cooling fraction 198.

For this purpose, the first fraction 194 is expanded in a sixth static expansion valve 200 down to a pressure below 2 bars which causes its cooling down to a temperature of −140° C. It is then heated up by heat exchange with the head stream 146 in the first heat exchanger 74 up to a temperature above −120° C., in order to form a first heated-up fraction 202.

Also, the second fraction 196 is expanded in a seventh static expansion valve 204 down to a pressure below 2 bars, which lowers its temperature to below −140° C. The second expanded fraction is then heated up by heat exchange with the head stream 166 in the second reflux heat exchanger 82 up to a temperature above −130° C. in order to form a second heated-up fraction 206.

The third fraction 198 is expanded in a eighth static expansion valve 208 down to a pressure below 2 bars in order to produce a third expanded fraction 210 at a temperature below −140° C.

The expanded fractions 202, 206 and 210 are then mixed in order to form a stream 212.

The stream 212 is successively heated up in the additional heat exchange region 54, in the downstream heat exchange region 52, in the intermediate heat exchange region 50 and in the upstream heat exchange region 48 by heat exchange with the streams respectively flowing in these regions for forming a heated-up stream 214. The stream 214 is then reintroduced as a mixture into the cracked gas 22, upstream from the first compressor 38 in order to be compressed again in the compressors 38, 40.

The sampling of a portion of an intermediate liquid 136 and its expansion in static valves 200, 204, 208 therefore produces the frigories required for forming the reflux streams of the columns 68 and 80 and allows completion of the heat balance on the cold box 46, by forming a mixed cycle of the JOULE-THOMPSON type integrating the assembly 26 for compressing the cracked gases.

This particular arrangement of the treatment method and of the associated treatment installation 24 considerably simplifies the structure of the installation 24 by avoiding having to pump cryogenic fluids and by achieving better thermal integration.

In particular, the intermediate gas head stream 146 is not pumped towards the absorption column 80, but is redirected towards the heat exchange regions 54 to 48, which avoids connecting the column 68 to the column 80 through a cryogenic pump.

Also, the integrated exchanger 69 positioned in the column 68 allows the use of a single distillation column and therefore the reduction in the number of pieces of equipment in the installation.

Further, the demethanization columns 62, 68 produce respective bottom streams 14A, 14B which have different compositions, the subsequent fractionation in the deethanizer is improved by a reduction in the energy consumption.

In any case, the treatment installation 24 and the method applied in this installation 24 allow recovery of more than 99.5% by moles of the ethylene present in the cracked gas 22, with reduced energy consumption and a simplified structure installation, which has reduced setting-up and maintenance costs.

Further, the cooling of a fraction 104 of the compressed crude cracked gas stream 100 in the reboiling heat exchangers 64, 70 of the columns 62, 68 minimizes the energy required for this cooling and the number of pieces of equipment, since the same heat exchanger 64, 70 ensures the reboiling function of a column 62, 68 and cooling of the crude cracked gas.

The hydrogen-rich gas 170 stemming from the ethylene absorption column 80 is further advantageously treated in order to recover a hydrogen-rich stream 18 by allowing the excess of hydrogen-rich treated gas 170 from the column 80 to be optionally expanded through a turbine 92 in order to generate a cold product which may be heated up in the cold box 46.

In one alternative, at least two regions among the upstream heat exchange region 48, the intermediate heat exchange region 50, the upstream heat exchange region 52 and the additional heat exchange region 54 are positioned in separate heat exchangers, which are not integrated within the cold box 46.

In one alternative, each of the regions 48, 50, 52, 54 is positioned in a specific heat exchanger.

What is claimed is:

1. A method for treating a cracked gas stream stemming from a hydrocarbon pyrolysis installation, comprising the following steps:
    upstream cooling and partial condensation of a crude cracked gas stream in at least one upstream heat exchange region;
    separating the partly condensed crude gas stream in at least one upstream separator in order to recover an upstream liquid and an upstream cracked gas stream;
    introducing the upstream liquid into an upstream demethanization column for recovering at the head of the upstream column, an upstream head stream rich in methane and, at the bottom of the upstream column, a first liquid stream rich in $C_2^+$ hydrocarbons;
    intermediate cooling and partial condensation of the upstream cracked gas stream in at least one intermediate heat exchange region;
    separating the partly condensed upstream cracked gas stream in at least one intermediate separator for recovering at least one intermediate liquid and one intermediate cracked gas stream;
    introducing the or each intermediate liquid into an intermediate demethanization column in order to recover at the head of the intermediate column, an intermediate head stream, and at the bottom of the intermediate column, a second liquid stream rich in $C_2^+$ hydrocarbons;
    introducing at least one portion of the upstream head stream from the upstream column into the intermediate column;
    downstream cooling and partial condensation of the intermediate cracked gas stream in at least one downstream heat exchange region;
    separating the intermediate partly condensed cracked gas stream in a downstream separation assembly for recovering a downstream liquid and a downstream treated gas stream;
    introducing the downstream liquid into the intermediate demethanization column (68),
    wherein the method comprises the following steps:
    sampling a portion of an intermediate liquid from an intermediate separator and cooling of the sampled portion in an additional heat exchange region;
    expansion of at least one first cooling fraction obtained from the sample portion and putting the first expansed cooling fraction in a heat exchange relationship with the intermediate head stream in a first head heat exchanger for at least partly condensing the intermediate head stream;
    separating the intermediate partly condensed head stream in a first reflux separator in order to form a liquid reflux stream introduced into the intermediate column by gravity flow, and a first combustible gas stream; and
    expansion and heating-up of the first combustible gas stream by having it pass in at least one region among the additional heat exchange region, the downstream heat exchange region, the intermediate heat exchange region, and the upstream heat exchange region.

2. The method according to claim 1, wherein the intermediate column includes an integrated heat exchanger, said or each intermediate liquid being introduced below the integrated heat exchanger, the upstream liquid being introduced above the integrated heat exchanger.

3. The method according to claim 1, further comprising a step for forming the crude cracked gas stream by compression of a cracked gas stemming from the pyrolysis installation in at least one compression apparatus, the method further comprising the following steps:
    heating up the first cooling fraction in the first head heat exchanger in at least one region among the additional heat exchange region, the downstream heat exchange region, the intermediate heat exchange region and the upstream heat exchange region; and
    introducing the first cooling fraction heated up in the cracked gas upstream from or within the compression apparatus.

4. The method according to claim 1, wherein the first combustible gas stream from the first reflux separator is expanded in a first dynamic expansion turbine, and then heated up in at least one region among the additional heat exchange region, the downstream heat exchange region, the intermediate heat exchange region and the upstream heat exchange region, the method comprising a step for compressing again the first heated-up combustible stream in at least one first compressor coupled with the first dynamic expansion turbine.

5. The method according to claim 1, wherein the first combustible gas stream from the first reflux separator is expanded in a static expansion valve.

6. The method according to claim 1, wherein the downstream separation assembly includes an ethylene absorption column, the method further comprising the following steps:
    introducing the intermediate partly condensed cracked gas stream into the ethylene absorption column;
    recovering an additional head gas stream from the ethylene absorption column;
    expanding a second cooling fraction obtained from the portion sampled in the intermediate liquid, and
    putting the second expanded cooling fraction into a heat exchange relationship with the additional head stream in a second head heat exchanger in order to at least partly condense the additional head stream;
    introducing the partly condensed additional head stream into a second reflux separator in order to form a second liquid reflux stream introduced into the ethylene absorption column by gravity flow and a treated gas stream.

7. The method according to claim 6, further comprising the following steps:
- forming the crude cracked gas stream by compression of a cracked gas from the pyrolysis installation in a compression apparatus;
- heating up the second cooling fraction, downstream from the second head heat exchanger, in at least one region among the additional heat exchange region, the downstream heat exchange region, the intermediate heat exchange region and the upstream heat exchange region;
- introducing the second heated-up cooling fraction into the cracked gas from the pyrolysis installation, upstream from or within the compression apparatus.

8. The method according to claim 6, further comprising the following steps:
- expanding at least one first portion of the treated gas stream in at least one second dynamic expansion turbine;
- heating up after expansion the first portion of the treated gas stream in at least one region among the additional heat exchange region, the downstream heat exchange region, the intermediate heat exchange region and the upstream heat exchange region; and
- compressing the heated-up first portion in at least one second compressor coupled with the second dynamic expansion.

9. The method according to claim 6, further comprising a step for expanding at least one first portion of the treated gas stream in a static expansion valve.

10. The method according to claim 6, wherein at least one second portion of the treated gas stream is introduced into a hydrogen purification unit for producing a hydrogen-rich stream and an auxiliary combustible gas stream, and optionally a secondary stream rich in methane.

11. The method according to claim 1, wherein a third fraction of the sampled portion is expanded before being directly heated up in at least one region among the additional heat exchange region, the downstream heat exchange region, the intermediate heat exchange region and the upstream heat exchange region.

12. The method according to claim 1, further comprising the following steps:
- separating the crude cracked gas stream into a first crude cracked gas fraction and into a second crude cracked gas fraction;
- upstream cooling and partial condensation of the first crude cracked gas fraction in the upstream heat exchange region;
- cooling the second crude cracked gas fraction in an upstream reboiling exchanger, by heat exchange with an upstream reboiling stream from the upstream column, and then cooling the second crude cracked gas fraction in an intermediate reboiling exchanger by heat exchange with an intermediate reboiling stream from the intermediate column; and
- forming the partly condensed crude cracked gas stream by mixing the first cooled crude cracked gas fraction and the second cooled crude cracked gas fraction.

13. The method according to claim 1, wherein the temperature of the partly condensed crude cracked gas before its introduction into the upstream separator is below −25° C., in that the temperature of the partly condensed upstream cracked gas stream before its introduction into the intermediate separator is below −60° C., in that the temperature of the partly condensed intermediate stream before its introduction into the downstream separation assembly is below −115° C.

14. An installation for treating a cracked gas stream from a hydrocarbon pyrolysis installation of the type comprising:
- means for upstream cooling and partial condensation of a crude cracked gas stream comprising at least one upstream heat exchange region;
- means for separating the partly condensed crude cracked gas stream comprising at least one upstream separator for recovering an upstream liquid and an upstream cracked gas stream;
- an upstream demethanization column, and means for introducing the upstream liquid into the upstream column in order to recover at the head of the upstream column, an upstream head stream rich in methane and at the bottom of the upstream column, a first liquid stream rich in $C_2^+$ hydrocarbons;
- means for intermediate cooling and partial compensation of the upstream cracked gas stream comprising at least one intermediate heat exchange region;
- means for separating the upstream partly condensed cracked gas stream comprising at least one intermediate separator in order to recover at least one intermediate liquid, and an intermediate cracked gas stream;
- an intermediate demethanization column and means for introducing the or each intermediate liquid into the intermediate column in order to recover at the head of the intermediate column, an intermediate head stream, and at the bottom of the intermediate column, a second liquid stream rich in $C_2^+$ hydrocarbons;
- means for introducing at least one portion of the upstream head stream from the upstream column into the intermediate column;
- means for downstream cooling and partial condensation of the intermediate cracked gas stream comprising at least one downstream heat exchange region;
- means for separating the intermediate partly condensed cracked gas stream comprising a downstream separation assembly in order to recover a downstream liquid and a downstream treated gas stream;
- means for introducing the downstream liquid into the intermediate demethanization column;

wherein the installation comprises:
- means for sampling a portion of an intermediate liquid from an intermediate separator, and means for cooling the sampled portion comprising an additional heat exchange region;
- means for expanding at least one first cooling fraction obtained from the sampled portion and means for putting the first expanded cooling fraction in a heat exchange relationship with the intermediate head stream comprising a first head heat exchanger for at least partly condensing the intermediate head stream;
- means for separating the intermediate partly condensed head stream comprising a first reflux separator in order to form a reflux liquid stream introduced into the intermediate column and a first combustible gas stream; and
- means for heating up the first combustible gas stream comprising means for passing into at least one region among the additional heat exchange region, the downstream heat exchange region, the intermediate heat exchange region and the upstream heat exchange region.

15. The installation according to claim 14, further comprising:
- means for forming the crude cracked gas stream by compression of a cracked gas from the pyrolysis installation including at least one compression apparatus;
- means for heating up the first cooling fraction downstream from the first head heat exchanger comprising means for passing into at least one region among the additional heat exchange region, the downstream heat exchange region, the intermediate heat exchange region and the upstream heat exchange region; and means for introducing the heated-up first cooling fraction into the cracked gas upstream from or within the compression apparatus.

16. The installation according to claim 14, wherein the downstream separation assembly includes an ethylene absorption column, the installation comprising:

means for introducing the intermediate cracked gas stream into the ethylene absorption column;

means for recovering an additional head gas stream from the ethylene absorption column;

means for expanding a second cooling fraction obtained from the sampled portion;

means for putting the second expanded cooling fraction in a heat exchange relationship with the additional head stream comprising a second head heat exchanger for at least partly condensing the additional head stream; and means for separating the additional partly condensed head stream comprising a second reflux separator for forming a second liquid reflux stream introduced into the ethylene absorption column and a treated gas stream.

17. The installation according to claim 14, further comprising:

means for forming the crude cracked gas stream by compression of a cracked gas from the pyrolysis installation including at least one compression apparatus;

means for heating up the second cooling fraction, downstream from the second head heat exchanger, comprising means for passing into at least one region among the additional heat exchange region, the downstream heat exchange region, the intermediate heat exchange region and the upstream heat exchange region; and means for introducing the second heated-up cooling fraction into the cracked gas from the pyrolysis installation, upstream from or within the compression apparatus.

* * * * *